(12) United States Patent
Haque

(10) Patent No.: US 12,084,644 B1
(45) Date of Patent: Sep. 10, 2024

(54) BIO-GROWTH CHAMBER WITH ROTARY MOTION AND HEATING SYSTEM AND RELATED METHODS

(71) Applicant: KING FAISAL UNIVERSITY, Al-Ahsa (SA)

(72) Inventor: Md Azizul Haque, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/409,771

(22) Filed: Jan. 10, 2024

(51) Int. Cl.
| | |
|---|---|
| C12M 1/00 | (2006.01) |
| C12M 1/06 | (2006.01) |
| C12M 1/12 | (2006.01) |
| C12M 1/34 | (2006.01) |

(52) U.S. Cl.
CPC ............ *C12M 23/34* (2013.01); *C12M 23/06* (2013.01); *C12M 23/38* (2013.01); *C12M 27/02* (2013.01); *C12M 29/14* (2013.01); *C12M 41/16* (2013.01); *C12M 41/42* (2013.01)

(58) Field of Classification Search
None
See application file for complete search history.

(56) References Cited

U.S. PATENT DOCUMENTS 1,848,957 A * 3/1932 Ladd et al. ............ A23C 3/031
366/302

FOREIGN PATENT DOCUMENTS

| | | | | |
|---|---|---|---|---|
| CN | 103589638 A | * | 2/2014 | ............ C12M 23/34 |
| CN | 205088239 U | | 3/2016 | |
| CN | 105670922 A | * | 6/2016 | |
| CN | 205668990 U | | 11/2016 | |
| CN | 205953997 U | | 2/2017 | |
| CN | 206359517 U | | 7/2017 | |
| CN | 207108840 U | | 3/2018 | |
| CN | 108913545 A | | 11/2018 | |
| CN | 111234568 A | * | 6/2020 | |
| CN | 113151088 A | * | 7/2021 | |
| KR | 10193603 B1 | | 4/2019 | |

OTHER PUBLICATIONS

Brand: Dhruv Fabrotech, Bio Fertilizer Fermenter, www.indiantradebird.com.
Ramy Hamouda1, Adel Bahnasawy, Samir Ali and El-Shahat Ramadan, Some Physical and Chemical Properties of Bio-fertilizers, ISSN: 2593-9173.

\* cited by examiner

*Primary Examiner* — William H. Beisner
(74) *Attorney, Agent, or Firm* — Nath, Goldberg & Meyer; Joshua B. Goldberg

(57) ABSTRACT

A growth chamber system includes a power source and an inner chamber. An access opening is included to the inner chamber. An outer chamber surrounds at least one wall of the inner chamber. A temperature sensor is included which monitors the temperature inside the inner chamber. A heater and pump are fluidly connected to the outer chamber and a working fluid is circulated by the pump through the heater and outer chamber such that an increase in temperature of the working fluid produces a temperature increase within the inner chamber by contact of the working fluid with an outer surface with at least one wall of the inner chamber. A rotor blade is positioned within the inner chamber and connected to an electric motor. At least one controller is included and connected to the fluid heater, pump, and electric motor and configured to control temperature and rotation speed.

15 Claims, 4 Drawing Sheets

BIO-GROWTH CHAMBER WITH ROTARY MOTION AND HEATING SYSTEM AND RELATED METHODS

BACKGROUND

Field

The disclosure of the present patent application relates to biological growth chambers, and particularly to a biological growth chamber system providing heating and rotary motion.

Description of Related Art

Bio-fertilizer growth chambers are devices used in the field of bio-chemistry, molecular biology, bacteriology, and organic farming. A bio-fertilizer growth chamber is a device inside which the temperature of liquids can be controlled based on the application. In certain biochemistry and other biological research facilities, continuous motion is required to induce and keep a test sample in continuous agitation in the desired temperature (below or above ambient temperature) for a period of time without causing any precipitation, as some chemical solutions and bacteria cultures have a tendency to precipitate if kept in a static system. This system is widely used in large quantity bacterial growth and screening, enzymatic saccharification, extraction procedures, fermentation, yeast and fungi culture, cell culture, and cell aeration. The system results in increasing solubility rates, hybridization, chemical mixing in controlled conditions, cellulose separation, and mercerization etc.

Continuous motion not only prevents precipitation but also ensures circulation of solvents over all the regions of test samples, which ensures better mixing. Production of bacteria in large quantity can be difficult and expensive, due to the size and cost of currently available growth systems, as well as the availability of such systems primarily in first world countries and the need to transport such currently available systems to other regions of the world. A need therefore exists for a bio-fertilizer growth system that is capable of providing heating and rotary motion in controlled conditions while remaining cost-effective and portable. Thus, a bio-fertilizer growth system solving the aforementioned problems is desired.

SUMMARY OF THE INVENTION

The growth chamber system disclosed herein includes a power source and an inner chamber defining a sample enclosure. An access opening is included through which a test sample is placed within the inner chamber. An outer chamber surrounds one or more walls of the inner chamber. A temperature sensor is included which monitors the temperature inside the inner chamber. A heater and pump are fluidly connected to the outer chamber and a working fluid is circulated by the pump through the heater and outer chamber such that an increase in temperature of the working fluid produces a temperature increase within the inner chamber by contact of the working fluid with an outer surface with at least one wall of the inner chamber. A rotor blade is positioned within the inner chamber and connected to an electric motor. At least one controller is included and connected to the fluid heater, pump, and electric motor. The at least one controller is configured to control temperature within the inner chamber, temperature of the working fluid, and a rotation speed of the electric motor.

In an embodiment, the inner chamber includes a first cylindrical sidewall and a first base. The outer chamber includes a second cylindrical sidewall and a second base. An annular seal having an inner circumference is connected to the first cylindrical sidewall of the inner chamber and an outer circumference of the ring-shaped seal is connected to the second cylindrical sidewall of the outer chamber.

In an embodiment, the inner chamber and outer chamber are formed of aluminum, and the working fluid is water. The volume of the inner chamber is approximately 22 liters. The internal temperature ranges up to about 42° C. The whole system is operated within approximately a 210-230V and 50-60 Hz power source.

In an embodiment, the access opening includes a fixed hood and a folding hood joined by hinges, the folding hood is moved between a closed position and an open position to allow access to the inner chamber.

In an embodiment, the inner chamber includes at least one first sidewall, and the outer chamber includes at least one second sidewall, a base, and an upper seal. The upper seal is joined to the at least one first sidewall and the at least one second sidewall.

In an embodiment, a heater chamber houses the heater. The heater chamber is positioned outside of the inner chamber and outer chamber, and is in fluid connection with the outer chamber pump through one or more pipe connections.

In an embodiment, the at least one controller includes a liquid crystal display and/or control switches.

In a further embodiment, a method of cultivating a sample within a growth chamber is provided. The method includes placing a biological sample within an inner chamber through an access opening wherein the inner chamber includes at least one first sidewall. A working fluid is circulated using a pump through an outer chamber, the outer chamber including at least one second sidewall. The working fluid contacts an outer surface of the at least one first sidewall and an inner surface of the at least one second sidewall. The working fluid is heated by a heater, whereby a change in temperature of the working fluid causes a change in temperature within the inner chamber through contact of the working fluid with an outer surface of the one or more first sidewalls.

The method includes agitating the biological sample within the inner chamber using a rotor connected to an electric motor. At least one controller is used for controlling the heater, pump and rotor motor and hence temperature of the working fluid, temperature of the inner chamber, and rotation speed of the rotor.

These and other features of the present subject matter will become readily apparent upon further review of the following specification.

BRIEF DESCRIPTION OF DRAWINGS

Similar reference characters denote corresponding features consistently throughout the attached drawings.

DETAILED DESCRIPTION

The disclosure herein relates to a highly effective and cost-efficient bacterial growth system. A significant decrease in production cost has been achieved (the cost being around 7 times less than typical growth systems). The internal volume is approximately 22 liters. The terms "approximately" or "about" as used herein with regards to a quantitative value refer to the specific nominal value as well as a ±10% variation from the nominal value unless otherwise indicated or inferred. In addition, the term "at least one" as used herein generally means "one or more" and the two terms are used interchangeably.

The system can produce about 15 liters of bio-fertilizer at one production time. An embedded heating system is included and can be regulated from ambient temperature to about 42° C. The whole system is operated by an approximately 210-230V and 50-60 Hz power source. This makes the system user friendly so that farmers can easily operate the setup at any load conditions in rural areas, such as those of Bangladesh.

Figure 1:
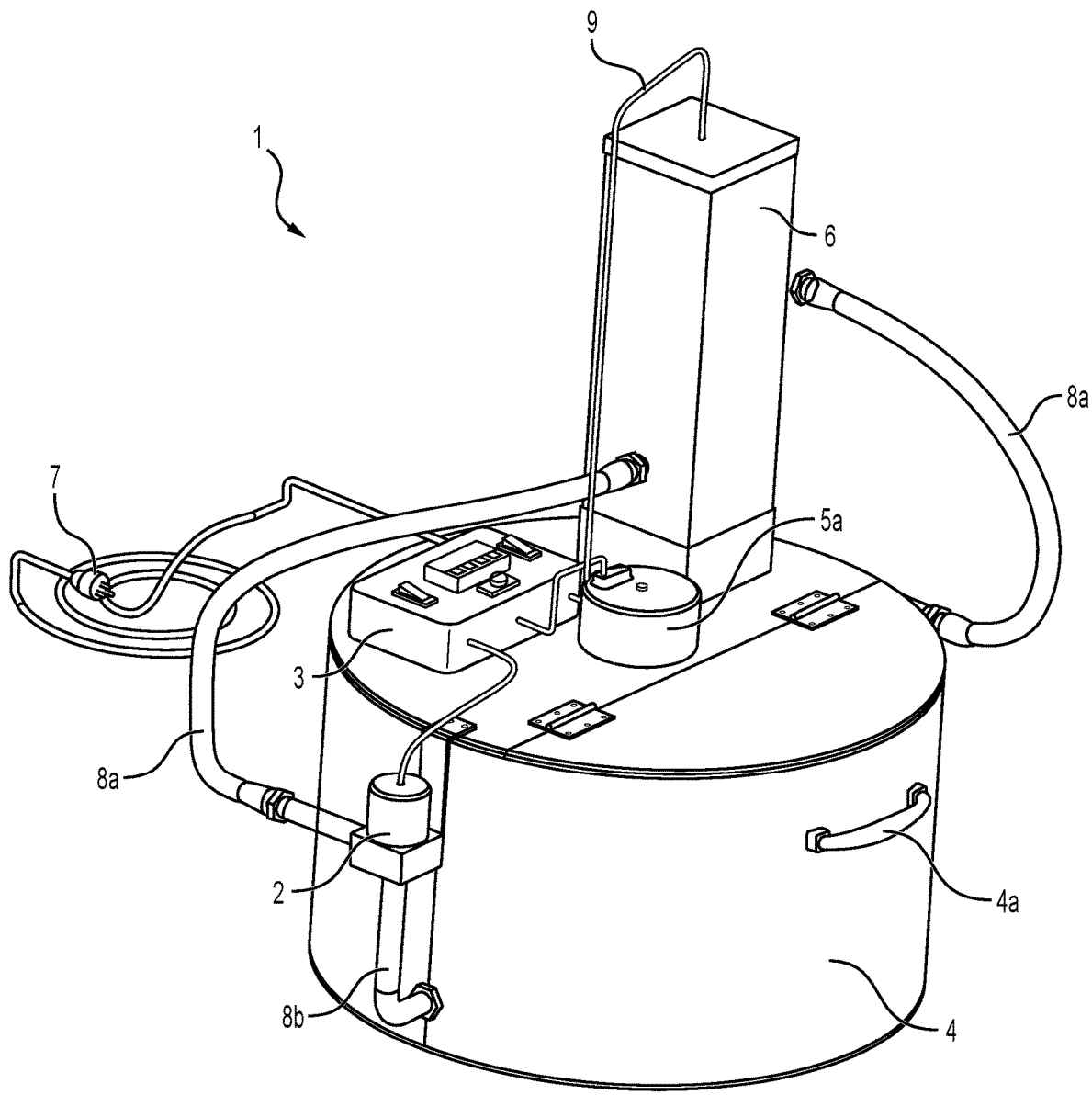
FIG. 1 is a perspective view of a growth chamber system.

FIG. 1 shows the growth chamber system 1 including a pump 2, controller 3, housing 4, rotor pump 5a, and heater 6. A power source 7 is included, shown as a wall outlet plug, while it should be understood that other power sources may be included and/or used such as a battery, solar panels and the like. Flexible piping sections 8a connect the heater 6 to the housing 4 and the pump 2 to the heater 6. Rigid piping section 8b connects housing 4 to the pump 2. Handles 4a are included in housing 4 for ease of portability of the growth chamber system 1.

Figure 2A:
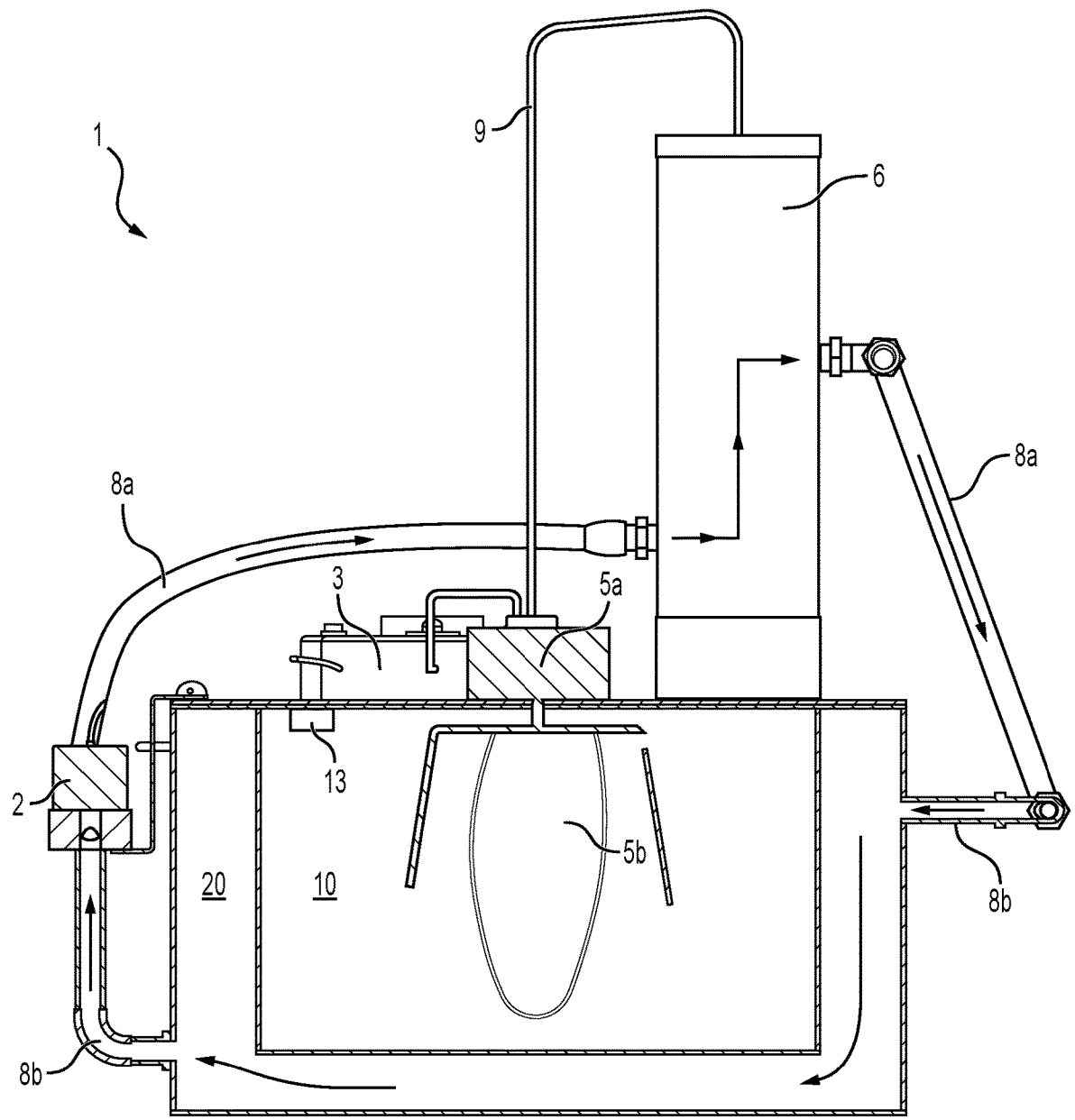
FIG. 2A is a side cutaway view of a growth chamber system.

With reference to FIG. 2A, the growth chamber system 1 includes an inner chamber 10 defining a sample enclosure. An outer chamber 20 surrounds inner chamber 10. A temperature sensor 13 is included which monitors the temperature inside the inner chamber 10. Temperature sensor 13 may be, for non-limiting example, a negative temperature coefficient (NTC) 5k/3470 sensor with an operation range of about 0-100° C. and approximately +1° C. accuracy.

Heater 6 and pump 2 are fluidly connected to outer chamber 20 through piping connections 8a, 8b, and a working fluid, such as water, is circulated by pump 2 through outer chamber 20 and heater 6 such that an increase in temperature of the working fluid causes an increase in temperature of inner chamber 10 by heat exchange or contact of the working fluid with the walls of inner chamber 10. A rotor 5b is positioned within inner chamber 10 and connected to an electric motor 5a. At least one controller 3 is connected to the fluid heater 6, pump 2, temperature sensor 13, and electric motor 5a. Controller 3 is configured to control heater 6 and thus the temperature of the working fluid as well as temperature within the inner chamber 10. While at least one controller 3 is shown for the pump, motor, and heater, it should be understood that individual controllers may be used for the respective components.

Figure 2B:
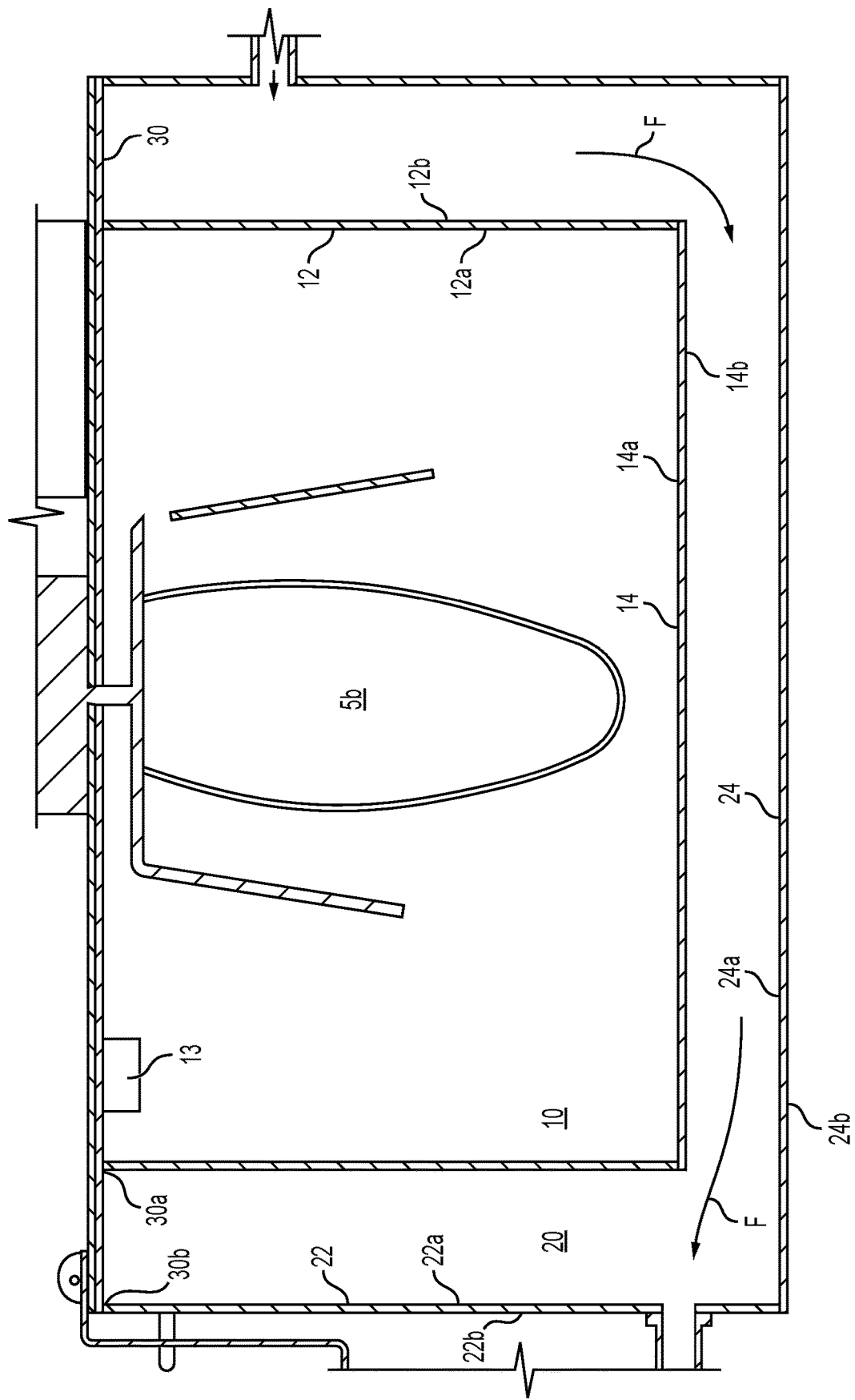
FIG. 2B is a side cutaway view of an inner chamber and outer chamber forming part of a growth chamber system.

Referring to FIG. 2B, in a non-limiting embodiment, inner chamber 10 includes at least one inner or "first" sidewall 12 and an inner, or "first," base 14. First sidewalls 12 include an inner surface 12a and an outer surface 12b. First base 14 includes an inner surface 14a and an outer surface 14b. Outer chamber 20 includes at least one outer, or "second," sidewall 22 having an inner surface 22a and outer surface 22b. Outer chamber 20 includes an outer, or "second," base 24 having an inner surface 24a and an outer surface 24b. In the non-limiting embodiment shown in FIG. 2B and FIG. 3, first sidewalls 12 and second sidewalls 22 each include a single cylindrical sidewall, respectively. In a non-limiting embodiment, the inner chamber 10 and outer chamber 20 are formed of aluminum, and the volume of the inner chamber 10 is approximately 22 liters.

An upper annular seal 30 is included having an inner circumference 30a that is joined to first sidewall 12 and an outer circumference 30b joined to second sidewall 22. Seal 30 may be joined to sidewalls 12 and 22 by, for example, welding. While sidewalls 12 and 22 can be cylindrical, circular or ellipsoidal, it should be understood that other shapes for the at least one first sidewall 12 and at least one second sidewall 22 may be provided in keeping with the teachings herein, such as walls forming a polyhedron or other shape. Still referring to FIG. 2B, as the working fluid flows through the outer chamber 20, shown by arrows F, the working fluid makes contact with outer surface 12b of the at least one first sidewall 12 and outer surface 14b of first base 14, as well as inner surface 22a of sidewalls 22 and inner surface 24a of base 24. The working fluid thus can exchange heat with the various surfaces, causing a change in temperature to occur due to the heat exchange.

Figure 3:
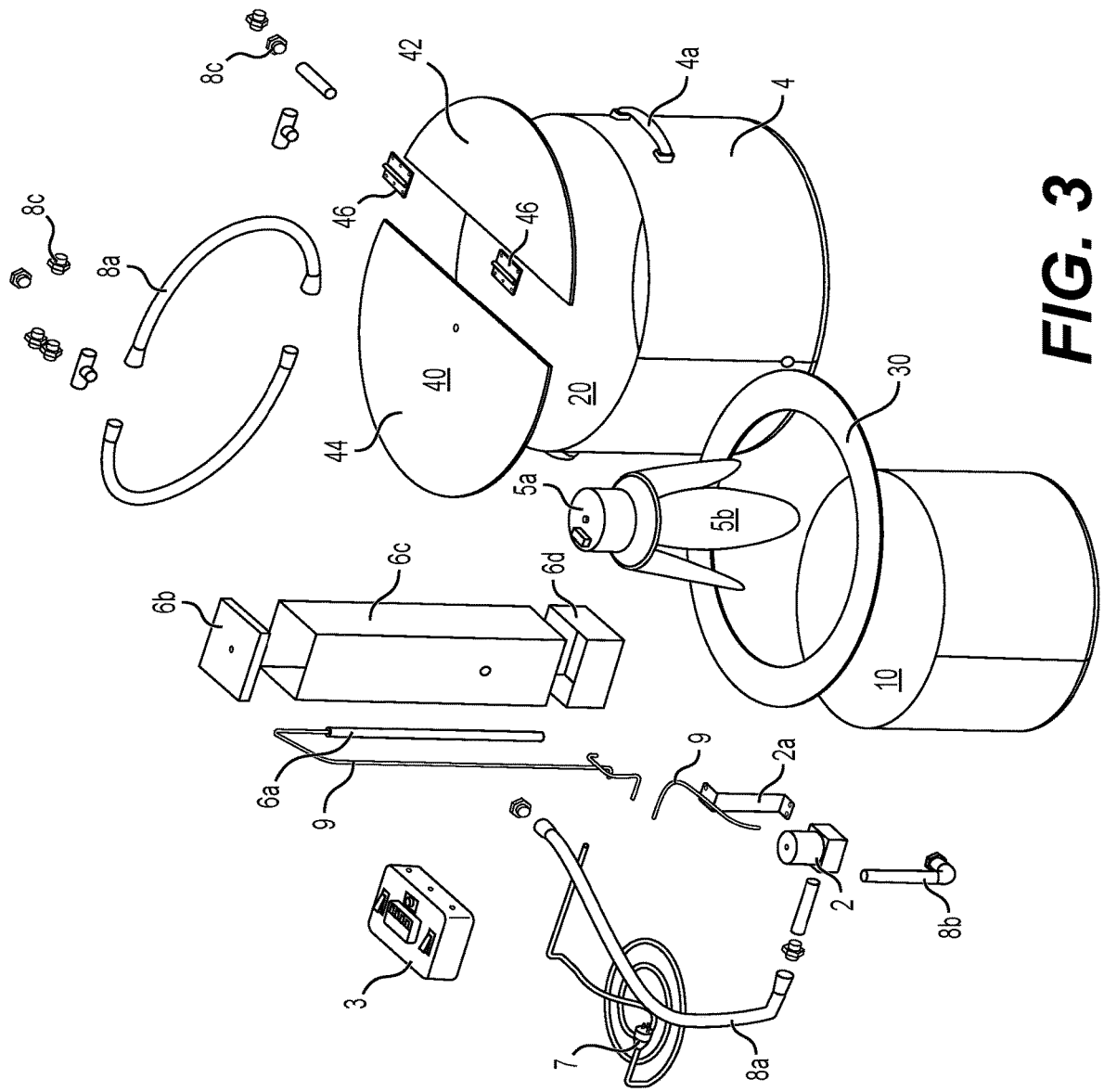
FIG. 3 is an exploded perspective view of a growth chamber system.

Turning to FIG. 3, an access opening 40 is included through which a test sample can be placed within the inner chamber 10. In a non-limiting embodiment, the access opening includes a fixed hood 44 and a folding hood 42, with the fixed hood 44 and the folding hood 42 joined together by hinges 46. The folding hood 42 is configured to move between a closed position and an open position to allow access to the contents of the inner chamber 10. Additional details of growth chamber system 1 include resistance heater 6a, which may be for example an AC 200 watts resistance heater. A heater chamber 6c is shown having hood 6b and chamber holder 6d for containment of resistance heater 6a. Joints 8c are included for connecting flexible pipe sections 8a and rigid piping sections 8b. A pump support 2a is included for attaching pump 2 to housing 4.

As shown in FIG. 1 and FIG. 3, controller 3 may include a combination of an LCD display and control switches for convenient operation and setup. Controller 3 includes a temperature controller having a solid state relay (SSR) to realize a larger heating power rate, as well as an optional proportional integral derivative (PID) control. Example controller properties further include a 350V AC 7.5 A load for output and 20 mA/10V DC max load for SSR drive output.

The growth chamber system disclosed herein incorporates a unique liquid heating system that helps to provide heat on the sides and base of an inner sample chamber and the included rotor helps to mix liquid bio-fertilizer samples properly. The rotor further helps to prevent precipitation of bacteria while allowing for adjustments of the rotor blade speed based on required conditions. The wide range of temperature and motion variation makes the bacterial growth system disclosed herein flexible enough to handle bacteria of many types. Some endophytic bacteria such as *Klebsiella* sp., *Acinetobacter* sp., *Citrobacter* sp., *Serratia* sp., *Pseudomonas* sp., and *Bacillus* sp. can be grown in the chamber. These bacteria can assimilate nitrogen, solubilize phosphate, produce plant growth promoting hormones such as indole acetic acid, and perform ACC-deaminase activities. As a consequence, rice, tomato, brinjal, okra, maize, and potato plant growth can be triggered by such plant growth-promoting (PGP) bacterial strains in fields. Since the growth chamber system can be made available to researchers and farmers at very low cost and easily, it provides significant potential for acceleration of future research, farming, and industrial applications.

It is to be understood that the growth chamber is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

The invention claimed is:

1. A biological growth chamber system, comprising:
a power source;
an inner chamber defining a sample enclosure;
an access opening through which a test sample is placed within the inner chamber;
an outer chamber, wherein the outer chamber surrounds one or more walls of the inner chamber;
a temperature sensor which monitors a temperature inside the inner chamber;
a heater and pump fluidly connected to the outer chamber;
a working fluid circulated by the pump through the heater and outer chamber, wherein an increase in temperature of the working fluid produces a temperature increase within the inner chamber by contact of the working fluid with an outer surface of one or more walls of the inner chamber;
a rotor blade positioned within the inner chamber, wherein the rotor blade is connected to an electric motor; and
at least one controller connected to the heater, pump, electric motor, the at least one controller and the power source, the at least one controller being configured to control the temperature within the inner chamber, a temperature of the working fluid, and a rotation speed of the electric motor,
wherein the access opening comprises a fixed hood and a folding hood joined by hinges, wherein the folding hood is movable between a closed position and an open position to allow access to the inner chamber.

2. The biological growth chamber system as recited in claim 1, wherein the inner chamber comprises a first cylindrical sidewall and a first base.

3. The biological growth chamber system as recited in claim 2, wherein the outer chamber comprises a second cylindrical sidewall and a second base, and an annular seal having an inner circumference connected to the first cylindrical sidewall and an outer circumference connected to the second cylindrical sidewall.

4. The biological growth chamber system as recited in claim 3, wherein, during circulation, the working fluid contacts an outer surface of the first cylindrical sidewall, an outer surface of the first base, and an inner surface of the second cylindrical sidewall and an inner surface of the second base.

5. The biological growth chamber system as recited in claim 1, wherein the inner chamber and the outer chamber are formed of aluminum.

6. The biological growth chamber system as recited in claim 1, wherein the working fluid is water.

7. The biological growth chamber system as recited in claim 1, wherein a volume of the inner chamber is about 22 liters.

8. The biological growth chamber system as recited in claim 1, wherein the inner chamber includes at least one first sidewall, and
wherein the outer chamber includes at least one second sidewall, a base, and an upper seal, and the upper seal is joined to the at least one first sidewall and the at least one second sidewall.

9. The biological growth chamber system as recited in claim 1, further comprising a heater chamber housing the heater.

10. The biological growth chamber system as recited in claim 9, wherein the heater chamber is positioned outside of the inner chamber and outer chamber, and is in fluid connection with the outer chamber and pump through one or more pipe connections.

11. The biological growth chamber system as recited in claim 1, wherein the at least one controller includes a liquid crystal display.

12. The biological growth chamber system as recited in claim 1, wherein the at least one controller includes control switches.

13. The biological growth chamber system as recited in claim 1, wherein the temperature within the inner chamber ranges up to about 42° C.

14. The biological growth chamber system as recited in claim 1, wherein the power source is operated within approximately 210-230V and 50-60 Hz.

15. A method of cultivating a biological sample within a growth chamber, the method comprising:
placing the biological sample within an inner chamber through an access opening, wherein the inner chamber includes at least one first sidewall;
circulating a working fluid using a pump through an outer chamber, the outer chamber including at least one second sidewall, wherein the working fluid contacts an outer surface of the at least one first sidewall and an inner surface of the at least one second sidewall;
heating the working fluid with a heater, whereby a change in temperature of the working fluid causes a change in a temperature within the inner chamber through contact of the working fluid with an outer surface of the at least one first sidewall;
agitating the biological sample within the inner chamber using a rotor connected to an electric motor; and
controlling the temperature of the working fluid, the temperature of the inner chamber, and a rotation speed of the rotor using at least one controller
wherein the access opening comprises a fixed hood and a folding hood joined by hinges, wherein the folding hood is movable between a closed position and an open position to allow access to the inner chamber.

* * * * *